(12) United States Patent
Castanas (10) Patent No.: US 7,358,379 B2
(45) Date of Patent: Apr. 15, 2008

(54) STEROID CONJUGATES, PREPARATION THEREOF AND THE USE THEREOF

(75) Inventor: Elias Castanas, Heraklion (GR)

(73) Assignee: Bionature E.A. Limited, Engomi, Nicosia (CY)

( * ) Notice: Subject to any disclaimer, the term of this patent is extended or adjusted under 35 U.S.C. 154(b) by 0 days.

(21) Appl. No.: 11/398,022

(22) Filed: Apr. 4, 2006

(65) Prior Publication Data

US 2006/0178295 A1    Aug. 10, 2006

Related U.S. Application Data

(63) Continuation of application No. 10/522,215, filed as application No. PCT/IB03/02785 on Jul. 14, 2003.

(30) Foreign Application Priority Data

Jul. 16, 2002    (GR) .................................. 020100335

(51) Int. Cl.
    C07J 1/00    (2006.01)
(52) U.S. Cl. ...................... 552/502; 552/500; 552/544; 552/588; 530/345; 530/362
(58) Field of Classification Search ................. 552/500, 552/544, 588, 502; 530/345, 362
    See application file for complete search history.

(56) References Cited

U.S. PATENT DOCUMENTS

| | | | |
|---|---|---|---|
| 4,215,102 | A | 7/1980 | Lee |
| 4,960,790 | A | 10/1990 | Stella et al. |
| 5,157,049 | A | 10/1992 | Haugwitz et al. |
| 5,248,796 | A | 9/1993 | Chen et al. |
| 5,945,279 | A | 8/1999 | Power et al. |
| 6,372,712 | B1 | 4/2002 | Briesewitz et al. |
| 6,416,737 | B1 | 7/2002 | Manolagas et al. |
| 6,740,304 | B2 | 5/2004 | Larsen et al. |
| 2004/0072776 | A1* | 4/2004 | Gleave et al. ............... 514/44 |
| 2005/0234027 | A1* | 10/2005 | Bothe et al. ................ 514/177 |

FOREIGN PATENT DOCUMENTS

| | | |
|---|---|---|
| EP | 1 104 667 | 6/2001 |
| GB | 2 068 973 | 8/1981 |
| WO | WO 93/02691 | 2/1993 |
| WO | WO 99/13914 | 3/1999 |
| WO | WO 01/82910 | 11/2001 |

OTHER PUBLICATIONS

Brann, et al.(1995) J. Steroid Biochem. Mol. Biol. 52, 113-133.
Grazzini, et al. (1998) Nature 392, 509-512.
Wehling, M. (1997) Annu Rev Physiol 59, 365-93.
Nadal, A. et al. (1998) FASEB J. 12, 1341-1348.
Nemere, I., et al. (1998) Biochem. Biophys. Res. Commun. 248, 443-449.
Jensen, E.V. (1996) Ann. N.Y. Acad. Sci. 748, 1-17.
Kumar, M.V. et al. (1998) Prog. Nucleic Acid Res. Mol. Biol. 59, 289-306.
Benten, P.W. et al. (1997) FEBS Lett 407, 211-214.
Benten, P.W., et al. (1999) Mol. Biol. Cell 10, 3113-23.
Lieberherr, M. et al. (1994) J. Biol. Chem. 269, 7217-7223.
Gorczynska, E. et al. (1995) Endocrinology 136, 2052-9.
Armen, T.A. et al. (2000) J. Cell Biochem 79, 620-7.
Lyng, F.M. et al. (2000) Biol. Reprod 63, 736-47.
Koukouritaki, S.B., et al. (1997) J Cell Biochem 65, 492-500.
Horoszewicz, J.S. et al. (1983) Cancer Res. 43, 1809-1818.
Mosmann T. (1973) J. Immunol. Methods 65, 53-63.
Bradford, M.M. (1976) Anal. Biochem. 72, 248-254.
Golenhofen, N. et al. (1995) Kidney Int. 48, 1837-45.
Auger, K.R. et al. (1989) Cell 57, 167-175.
SIngh S.S., et al. (1996) Biochemistry 35, 16544-16549.
Benard, V., et al. (1999) J. Biol. Chem 274, 13198-13204.
Simionescu L et al: "The development of a radioimmunoassay system for testosterone (T) and dihydrotestosterone (DHT). Part 2. The preparation of antisera to T." Endocrinologie. Romania Jul.-Dec. 1990, vol. 28, No. 3-4, Jul. 1990, pp. 107-125, XP008014908, ISSN: 0253-1801.
Ramirez V D et al: "Membrane receptors for estrogen, progesterone, and testosterone in the rat brain: fantasy or reality." Cellular and Molecular Neurobiology. United States APR 1996, vol. 16, No. 2, Apr. 1996, pp. 175-198, XP008014894 ISSN:0272-4340, table 1.
Benten W P et al "Functional testosterone receptors in plasma membrances of T cells." The FASEB Journal: Official Publication of the Federation of American Societies for Experimental Biology. United States JAN 1999, vol. 13, No. 1 Jan. 1999, pp. 123-133, XP002234365, ISSN: 0892-6638, cited in the application figures 1,3.
Kampa Maeilena et al: "The human prostate cancer cell line LNCap bears functional membrane testosterone receptors that increase PSA secretion and modify actin cytoskeleton." The FASEB Journal: Official Publication of the Federation of American Societies for Experimental Biology. United States SEP 2002, vol. 16, No. 11, Sep. 2002, pp. 1429-1431, XP002234364, ISSN: 1530-6860, abstract; figure 3.
Papakonstanti Evangelia A et al: "A rapid, nongenomic, signaling pathway regulates the actin reorganization induced by activationo f membrane testosterone receptors." Molecular Endocrinology (Baltimore, MD.) May 2003, vol. 17, No. 5, May 2003, pp. 870-881, XP 0008024806, ISSN: 0888-8809, abstract.

* cited by examiner

Primary Examiner—David Lukton
(74) Attorney, Agent, or Firm—Robert L. Buchanan, Esq.; Edwards Angell Palmer & Dodge LLP; Peter C. Lauro, Esq.

(57) ABSTRACT

Conjugates comprising one or more steroids conjugated with one or more mammalian proteins are disclosed. The conjugates are useful for diagnosis or treatment of solid cancer and hematological malignancies. Further the conjugates exhibit a synergistic action together with a cytoskeleton-acting drug such as Taxol®, which enable the treatment of cancers that otherwise would be non-responsive to Taxol®.

18 Claims, 9 Drawing Sheets

Testosterone    Estradiol    Progesterone

STEROID CONJUGATES, PREPARATION THEREOF AND THE USE THEREOF

This application is a continuation, pursuant to 37 C.F.R. §1.53(b)(1), of application Ser. No. 10/522,215, filed Apr. 7, 2005, which is a U.S. national phase application of international application no. PCT/IB2003/002785, filed on Jul. 14, 2003, designating the United States and published in English as publication no. WO 2004/006966 A1 on Jan. 22, 2004, which in turn claims priority to GR 20020100335, filed Jul. 16, 2002. The entire disclosure of each of the aforementioned applications is incorporated herein by this reference.

The present invention relates to new steroid conjugates that are useful for the diagnosis and treatment of solid cancers and hematological malignancies.

Further the invention relates to combinations of said steroid conjugates with cytotoxic agents showing synergistic effects in the diagnosis and treatment of cancer.

BACKGROUND FOR THE INVENTION

Classical steroid hormone action is mediated through intracellular steroid hormone receptors. These proteins dimerize, after steroid binding, translocate to the nucleus, and exert specific nuclear transcription factor effects on specific steroid-sensitive genes [1]. In recent years, however, a number of studies indicate that, in addition to the above genomic action, steroids bear non-genomic effects, mediated in minutes, and implicating different pathways than those involved in classical steroid receptor action [2, 3]. Non-genomic steroid actions were, in addition, been found in cells not expressing classical steroid receptors. The above, non-genomic steroid receptor actions were attributed to another class of steroid receptors, found on membrane of cells, and being biochemically, immunologically and pharmacologically different from classical steroid receptors. Until now, non-genomic steroid effects were found for estradiol, cortisol, and testosterone, in animal tissues, usually not-expressing classical receptors [2-13]. Activation of these non-classical steroid sites, found on membranes of cells was the increase of the flux of extracellular calcium to the cytosol [8-10, 12, 14], and in some times, modifications of the cytoskeleton [7, 15]. In all cases, BSA-conjugated steroids were used as ligands for these extracellular (membrane) steroid sites, in order to identify these sites. Indeed, covalent binding of steroids with high (60 kD) molecular weight proteins makes these molecules to loose their lipid solubility (and therefore the property of translocating to the cell through the plasma membrane) and confines them with water solubility and the possibility of binding to specific steroid sites. Commercially available sources of these compounds are currently available (e,g, Sigma Chemical Co. St Louis, Mo., USA). Nevertheless, human applications of this membrane steroid receptor activation have not been described so far.

GB 2 068 973 A, disclose conjugates of a steroid and an immunogenic protein such as human serum albumin for use in compositions for increasing ovulation in cattle.

EP 1 104 677 A2 discloses conjugates of a protein and a low molecular weight compound, where steroids are mentioned as examples of such. Bovine serum albumin is mentioned as an example of a protein useable in such conjugates. If at least part of the low molecular compounds is cytostaticum and the protein is a tumor specific antibody, an enzyme or a lectin the conjugates may be used for treatment of cancer.

U.S. Pat. No. 6,372,712 B1 discloses synthetic bifunctional molecules containing a drug moiety and a presenter protein ligand. Steroids are mentioned as examples of a drug moiety and albumin is mentioned as a preferred example of a presenter protein. The conjugates may be used to enhance the binding affinity and/or specificity of the agent to its target. It is stated that the conjugates can be used for treatment of different diseases dependent on the type of drug moiety used, but there are no specific teachings on which diseases may be treated with which drug moiety.

WO 01/82910 A2 discloses therapy of cancer using a composition comprising progesterone and RU486 (Mifesterone) or derivatives thereof and a portion of HPV E2 protein for the treatment of cervical cancer or certain precancerous cervical lesions. The HPV E2 protein is known to be lethal for the cervical tissue and the connection with the steroid seems to enhance this effect. The steroid may be bound to a steroid carrier protein such as human serum albumin.

U.S. Pat. No. 4,215,102 A1 discloses a conjugate consisting of progesterone or estrogen, protein and a fluorochrome. The conjugates may be used for detection of steroid hormone receptors in excised human tissue sections.

WO 99/13914 A1 disclose the pharmaceutical compositions comprising therapeutic active substances having low aqueous solubility bound to a plasma protein fraction in controlled aggregation state in order to increase the soluble amount of the active substances and thereby increase the availability thereof.

WO 93/02691 A1 disclose a delivering system for glucocorticoids using a protein carrier molecule having a binding site for glucocorticoids and a binding site for the targeted cell population. There is not indicated particular indication for which pharmaceutical compositions comprising said delivering systems are useful but it may be used for conditions known to be treatable with glucocorticoids.

DESCRIPTION OF THE INVENTION

The invention is based on the discovery that steroid conjugated to a mammalian protein may surprisingly have a cytotoxic effect on cancer cells, even when neither the steroid nor the mammalian protein by itself exert any substantial cytotoxic effect.

Thus in one aspect the invention related to the use of one or more steroids thereof, which are not cytostaticum, conjugated with mammalian proteins for the manufacture of pharmaceutical compositions for the treatment of solid cancers or hematological malignancies.

The steroid may in principle be any steroid thereof having a cytostatic effect when conjugated to a soluble mammalian protein. The term "steroids" is according to the invention intended to comprise all natural and synthetic steroid hormones, their analogs and derivatives thereof such as sulphate and fatty acid esters, their precursors, metabolites and their analogs, which may be steroidal or not steroidal in structure.

As analogs the inventors contemplate all natural, semi-synthetic or synthetic polycyclic molecules, capable to bind to human membrane steroid receptors, their mixtures, precursors and metabolites.

In one preferred embodiment the steroid is a steroid capable of binding to a membrane associated steroid receptor.

As examples of suitable steroid according to the invention can be mentioned: glucocorticoids, cortisol, testoterone, estrogen, estradiol, progesterone and any known analogs thereof.

The mammalian protein may according to the invention in principle be any mammalian protein that is water soluble when conjugated to steroid.

The mammalian protein may be selected among globular proteins, plasma proteins, albumins, binders or antibodies of selective human tumoral cell antigens.

Albumins are preferred examples of proteins to be conjugated to steroids according to the invention.

Human albumins and bovine serum albumin (BSA) are examples of preferred proteins to be conjugated according to the invention.

Human albumins are particular preferred in case that the particular conjugate is intended for treatment of a human being.

The term protein is contemplated to comprise natural and non natural proteins. In this context non natural proteins are considered any protein that differs from a natural occurring protein in amino acid sequence, glycosylation pattern or chemical modifications. Non natural proteins may be provided using recombinant DNA technologies or by chemical modifications of natural proteins.

Non natural proteins provide the possibilities of modifying natural proteins in order to e.g. reduce the antigenicity in a intended host; insert a suitable hapten; increase the stability of the protein against e.g. oxidation; provide a suitable site at the protein for improved attachment of a steroid; provide a suitable way of producing the intended protein.

Non natural proteins are considered mammalian protein if they directly or indirectly are derived from natural mammalian proteins, such as by e.g. chemical modification of isolated natural protein, or by recombinant DNA technologies, where a gene encoding a mammalian protein is used in is original or in a modified form.

Natural proteins may be provided from a natural source or from tissue cultures of natural or recombinant cells provided by recombinant DNA technologies.

It is within the skills of the average practioner to provide a given suitable natural or non natural protein using known procedures.

If the steroid protein conjugates according to the invention is intended for use in a treatment regimen the protein is preferably selected so that it is not immunogenic in the intended subject for the treatment.

The conjugates according to the invention may be prepared by procedures that are known per se, wherein the steroid is attached to the protein. The attachment may be any attachment that provides for a stable conjugate, preferably a covalent attachment.

In addition to steroid further groups may be attached to the protein e.g. a labelling attached for diagnostic purposes e.g. a hapten, a coloured moiety, a fluorescent moiety, a radionuclid etc.

The covalent attachment of the steroid moiety to proteins will be made by the use of conventional methods (ex. attachment of a carboxy-methyl ether moiety, and the attachment to proteins by the action of carboxydiimide).

In order to increase the selectivity of the steroid-protein conjugates, different attachments of the steroid moiety to the protein will be made (ex. attachment trough addition of an acid group at carbon positions 1, 3, 7, 11 or 15 of the steroid—the list is not exclusive-).

According to the invention the conjugates may be used for treatment of solid cancers and haematological malignancies.

As examples of solid cancers can be mentioned: prostate adenocarcinoma (hormone sensitive and resistant) and its metastases (lymph node, bone etc.), breast cancer (hormone sensitive and resistant) and its metastases in any places (lymph node, bone etc.), phenochromocytomas and their metastases, bone tumors and their metastases brain tumors (neuroblastomas) etc. (the list is not exclusive).

As examples of haematological malignancies can be mentioned: Acute and chronic myeloid leukaemia, acute and chronic lymphoid leukaemia and lymphomas (B and T).

In principle the conjugates may be used for the treatment of the mentioned indications in any mammal in need for such a treatment.

As examples of mammals that may be treated using the conjugates according to the invention can be mentioned: human beings, cattle, dog, sheep, horse, goat, donkey, cat and monkeys. Preferably the conjugates are used for the treatment of humans.

In a preferred embodiment the conjugates according to the invention is used for the treatment of cancer or haematological malignancies in a human being.

For such treatment the conjugates may in principle be administered in any known administration form such as oral or rectal administration or by parenteral, percutaneous or intravenous injection, where parenteral, percutaneous or intravenous injection are preferred.

The dosages and regimens are generally to be determined in accordance to the discretion of the attending physician, taking due considerations to the patient's age, weight, condition etc.

Generally the daily dosages may be in the range of 1 mg/kg body weight to 100 mg/kg body weight, preferably in the range of 5 mg/kg body weight to 100 mg/kg body weight, more preferred in the range of 5 mg/kg body weight to 50 mg/kg body weight and most preferred in the range of 5 mg/kg body weight to 20 mg/kg body weight, and in a particular preferred embodiment the daily dosage is around 7 to 10 mg/kg body weight. The treatment is generally continued for up to 6 months, preferably in the range of 2 weeks to 6 months, more preferred in the range of 2 weeks to 3 months.

The pharmaceutical compositions may be administered at regular intervals during the period of treatment in order to maintain a satisfactory concentration of the active compound in the circulation, as the skilled person will appreciate. Thus the pharmaceutical composition according to the invention may be administered once or more times daily or even with regular intervals of one or more day e.g. every second day, according to the discretion of the attending physician taking due consideration to the treatment efficiency and the acceptance of the patient being treated.

Another aspect of the invention might take account the possible degradation of the conjugate according to the invention and the resulting liberation of free hormone.

In order to obtain this tumors bearing testosterone receptors, an antiandrogen may be added and the tumor treated using a steroid conjugate according to the invention where the conjugate is a testosterone protein conjugate.

In addition, for tumors bearing estrogen or progesterone receptors an antiestroge or an anti progestin respectively will replace the antitestosterone, while protein conjugated estrogens or progestins will replace testosterone protein conjugates.

In the same line of development, in any tissue in which membrane steroid receptors will be found the corresponding steroid conjugate with 10 times higher antisteroid agent and anticytoskeleton agents may be administered. It is within the skills of the average practioner to determine the optimal combination in a given situation using common skills and routine experimentation.

Thus in the aspect the pharmaceutical composition according to the invention may further comprise one or more antiandrogens in the case thae the steroid present in the administered conjugate is an androgen. Without wishing to be bound by any particular theory it is believed that the antiandrogens block classical androgen receptors, and thereby abolished the effect that hormones liberated from a conjugate might have.

Antiandrogens may be added in an amount up to 10 times higher amount than the amount of steroids in the conjugate administered, calculated on a molar basis.

In case that the steroid present on the steroid-protein conjugate is not an androgen but is estrogen or progesterone the antiandrogene may be replaced by an antiestrogen or an antiprogestine, respectively.

Antiandrogenes, antiestrogenes and antiprogestines will be known for the person skilled in the art.

As examples of antiandrogens can be mentioned Cyprotone acetate and flutamide. As examples of antiestrogens and anti progestines can be mentioned tamoxifene and RU486, respectively.

In another aspect the conjugates according to the invention is used for diagnostic purposes.

For the diagnostic use the specimen is contacted with the conjugate followed by detection of bound conjugate by any suitable technique.

In one embodiment the conjugate is used for diagnosis in vivo combined with an antiandrogen in order to achieve a pharmaceutical orchecthomy, and block any deleterious effect of free testosterone.

In this embodiment the conjugate is administered to the subject followed by detection of the binding of the conjugate to the target. For such an in vivo diagnostic use, a labelling is preferably attached to the conjugate e.g. a radionuclid or an electrondense compound functioning as a contrast agent for X-ray analysis.

In another embodiment the conjugate is used for diagnosis ex vivo. In principle any biological specimen may be tested for binding of conjugate to the specimen. For such application it may be advantageous if the conjugate is easy detectable, e.g. due to attachment of detectable groups or by using antibodies specific for the protein part of the conjugate.

The inventors have further found a synergy between the conjugate according to the invention and a cytoskeleton acting drug.

Thus in s further aspect the invention relates to a pharmaceutical composition comprising one or more steroids, which are not cytostaticum, conjugated with a mammalian protein and a cytoskeleton-acting drug.

The surprising synergy between the conjugate according to the invention and cytoskeleton acting drugs allow the treatment of solid cancers and haematological malignancies, which otherwise would be non responsive or only low or moderate responsive to cytoskeleton acting drugs, using this combination.

Thus in a further aspect the invention relates to the use of a pharmaceutical composition comprising one or more steroids, which are not cytostaticum, conjugated with a mammalian protein and a cytoskeleton-acting drug for the treatment of solid cancer or haematological malignancies.

The term "cytoskeleton acting drugs" is according to the invention used in the usual meaning. As examples of a cytoskeleton-acting drug can be mentioned Taxol® or Taxotere®.

The treatment using a combination of the conjugate according to the invention and a cytoskeleton-acting drug may be performed by administration of one pharmaceutical composition comprising both active compounds, or it may be performed by administration of separate pharmaceutical entities, one comprising the conjugate and another comprising the cytoskeleton acting drug.

The dosages and regimens of the conjugate and the cytoskeleton-acting drug are similar to the corresponding dosages and regimens applied if the particular conjugate and drug were administered separately.

If the conjugate and the cytoskeleton-acting drug and/or the antisteroid compound are administered as separate pharmaceutical compositions, they may conveniently be provided in a kit comprising these two pharmaceutical compositions.

Thus in a further embodiment the invention relates to a kit comprising:
  a pharmaceutical composition comprising one or more steroids, which are not cytostaticum, conjugated with a mammalian protein; and
  a pharmaceutical composition comprising a cytoskeleton acting drug, or
  one of an antiandrogen, an antiestrogen and an antiprogestin in case that the tumor is bearing testosteron-, estrogen- or progesterone-receptors, respectively.

In an even further embodiment the invention relates to a kit comprising:
  a pharmaceutical composition comprising one or more steroids, which are not cytostaticum, conjugated with a mammalian protein; and
  a pharmaceutical composition comprising a cytoskeleton acting drug, and
  one of an antiandrogen, an antiestrogen and an antiprogestin in case that the tumor is bearing testosteron-, estrogen- or progesterone-receptors, respectively.

The invention consists of the determination, production and use of membrane steroid receptors agonists, determined by the association binding of these molecules with membrane steroid receptor bearing cells.

The invention will use these molecules for the diagnosis and treatment of solid tumor and hematologic malignancies in humans.

The specific molecules will be used, according to the invention, for the production of diagnostic and therapeutic agents. They are protein-conjugated (BSA-conjugated, Human Serum Albumin (HSA)-conjugated, binders or antibodies of selective human tumoral cell antigens for example—the list is not exclusive-) steroids.

The invention will be used, as illustrated in the examples provided, to produce specific diagnostics in cases of solid tumors and hematological malignancies.

The action of membrane steroid receptors, as illustrated by the examples, being the modifications of actin cytoskeleton, and the potentiation and extension of the action of cytoskeleton-acting drugs (eg. Taxol®) makes membrane steroid receptor agonists an interesting class of potential drugs.

The inventors will therefore target the production of new drugs, capable for a specific and selective binding to a class of membrane steroid receptors, present, as illustrated in the provided examples, in selective malignancies, in view of a selective primary or adjuvant chemotherapy. In another aspect, these agents, used as chemotherapeutics, could be used, alone, in combination with antisteroid drugs or in association with other chemotherapeutics (ex. Taxol® or equivalent drugs), in order to prevent, or modulate the chemoresistance of selective tumors.

The inventors will determine the best mode of administration of these drugs (local or general, injectable or locally applied during interventions, etc).

The invention will now be further illustrated in more details in the following examples with reference to the enclosed figures. Other characteristics and advantages of the invention are given in the following examples, the references, which are hereby enclosed by reference, and the attached Figures.

It should be understood that the examples and figures are provided for illustration and should not be considered as limiting in any way.

EXAMPLES

Material and Methods

Cell Line

The human prostate cancer LNCaP cell line, originally isolated from a lymph node metastasis of prostate adenocarcinoma [16], was purchased from DSMZ (Braunschweig, Germany). Cells were cultured in RPMI 1640 medium supplemented with 10% heat inactivated fetal bovine serum (FBS) at 37° C. in a humidified atmosphere of 5% $CO_2$ in air. They were subcultured once a week and incubated in serum-free medium for 24 h before any experiment. All culture media were purchased from Gibco BRL (Life Technologies, Paisley, UK).

Cell number was assayed using the tetrazolium salt assay [17]. Cells were incubated for 3 h at 37° C. with the tetrazolium salt (3-(4,5 dimethylthiazol-2-yl)-2,5 diphenyl tetrazolium bromide, Sigma, St Louis, Mo.). Living cells reduced the dye to purple formazan seen as dark blue crystals. At the end of the incubation period they were dissolved with propanol-1 and the absorbance was measure at 575 nm, within one hour.

Detection of Membrane Androgen Receptors i. Binding Assays

Membrane Preparation

Cells, cultured in 150 $cm^2$ flasks without serum, were washed twice with phosphate-buffered saline (PBS), removed by scraping and centrifuged at 1500 rpm. Pelleted cells were homogenized by sonication in 50 mM Tris-HCl buffer pH 7.4 containing freshly added protease inhibitors (10 µg/ml PMSF and 1 µg/ml aprotinin). Unbroken cells were removed by centrifugation at 2500 g for 15 min. Membranes were obtained by centrifugation at 45,000 g for 1 hour, and washed once by the same buffer. Protein concentration was measured by the method of Bradford [18].

Binding Conditions

Saturation binding experiments were performed in a final volume of 0.1 ml, containing cell membranes at a final protein concentration of 2 mg/ml and at least 6 different concentrations of [$^3$H]testosterone (ranging 2-50 nM) without (total binding) or with (non-specific binding) a 100-fold molar excess of unlabelled androgen (DHT). For displacement binding experiments, cell membrane preparations at a final concentration of 2 mg/ml were incubated with 5 nM of [$^3$H]testosterone (specific activity 95 Ci/mmole, Amersham-Pharmacia, Buckinghamshire, UK) in the absence or in the presence of different concentrations of un unlabelled steroid (DHT, estradiol, progesterone, all from Sigma, St Louis, Mo.), ranging from $10^{-12}$ to $10^{-6}$ M. Non specific binding was estimated in the presence of 5 µM DHT. In both types of binding experiments, after an overnight incubation at 4° C., bound radioactivity was separated by filtration under reduced pressure through GF/B filters previously soaked in 0.5% polyethylenimine (PEI) in water and rinsed three times with ice-cold Tris-HCl buffer. Filters were mixed with 4 ml scintillation cocktail and the bound radioactivity was counted in a scintillation counter (Tricarb, Series 4000, Packard) with 60% efficiency for Tritium.

ii. Flow Cytometry

LNCaP cells, cultured in serum free medium for 24 hrs, were detached from the culture flask by scraping and suspended in PBS at a density of $10^6$ cells/ml. They were incubated at room temperature with $10^{-7}$ M testosterone-BSA-FITC conjugate for different periods of time (1 min to 1 hour). A thousand-fold BSA-FITC was used to determine non-specific binding. Cells were analysed by flow cytometry using a Coulter Epics L-MCL apparatus (Beckman-Coulter Inc. Foullerton Calif., USA) in a sample size of 10,000 cells gated on the basis of forward and side scatter. Testosterone3-(O-carboxymethyl)oxime-BSA-FITC (named testosterone-BSA-FITC), testosterone3-(O-carboxymethyl)oxime-BSA (named testosterone-BSA), estradiol6-(O-carboxymethyl) oxime-BSA-FITC (named estradiol-BSA-FITC), progesterone3-(O-carboxymethyl)oxime-BSA-FITC (named progesterone-BSA-FITC) and BSA-FITC were obtained from Sigma (St Louis, Mo.).

iii. Confocal Laser microscopy

LNCaP cells were allowed to grow on poly-L-lysine coated glass coverslips for at least 48 hours before culture medium was replaced with serum free medium. After a 24-hour period, cells were washed twice with PBS and incubated with Testosterone-BSA-FITC for 30 min in the presence or in the absence of DHT. As a negative control BSA-FITC was used. Cells were then washed twice with PBS and fixed with 2% PFA in PBS for 30 min. Coverslips were mounted on to slides using a 1:1 (v/v) mixture of glycerol and Vestashield (Vector, Burlingame, Calif.). Specimens were analysed using a confocal laser scanning microscope (CLSM) (Leica TCS-NT, Lasertechnik, Heidelberg, Germany).

Detection of Membrane Steroid Receptors in Paraffin-Embedden Tissue Preparations Tissue slides were prepared from paraffin blocks of formalin fixed tissue preparations. Three-four micron (μm) thick tissue sections were cut and put on on SuperFrost Plus slides (Kindler O GmbH, Freiburg, Germany), incubated at 56° C. for 2 h, washed six times with xylene (5 min each), followed by 96%, 80% and 70% ethanol for five minutes each, and finally with distilled water for 20 min. Tissue slides were then incubated in citrate buffer in a microwaves oven at 500 Watts, three times for 4.5 minutes each. Alternatively, slides were incubated at 40 C overnight to remove paraffin in a milder way. Then, they were washed in distilled water and Tris buffered saline (TBS, 10 mM, pH 7.4). Non-specific absorption of BSA was eliminated by a 10 min incubation with a 2% solution of BSA in TBS, followed by two washes with TBS. Slides were then incubated for 10 min with BSA-FITC conjugated steroids and washed with TBS. Coverslips were mounted on to slides using a 1/1 (v/v) mixture of glycerol and Vestashield (Vector, Burlingame, Calif.). Specimens were analysed using a confocal laser scanning microscope (CLSM) (Leica TCS-NT, Lasertechnik, Heidelberg, Germany).

Determination of Monomeric and Polymerized Actin

For measurements of the monomeric (Triton soluble) and polymerized (Triton insoluble) actin, LNCaP cells were incubated for 10 min with or without DHT or testosterone-BSA ($10^{-7}$ M). Then, 500 μl of Triton-extraction buffer (0.3% TritonX-100, 5 mM Tris, pH 7.4, 2 mM EGTA, 300 mM sucrose, 2 μM phalloidin, 1 mM PMSF, 10 μg/ml leupeptin, 20 μg/ml aprotinin, 1 mM sodium orthovanadate, and 50 mM NaF) were added, and the mixture was incubated for 5 minutes on ice. After removing the buffer, soluble proteins were precipitated with equal volumes of 6% PCA. The Triton-insoluble fraction remaining on the plate was precipitated with 1 ml of 3% PCA. Equal volumes of each fraction were subjected to SDS-polyacrylamide gel electrophoresis (SDS-PAGE). The resulting protein-bands were transferred onto nitrocellulose membrane, and the membrane was blocked with 5% nonfat dry milk in TBS-T (20 mM Tris pH 7.6, 137 mM NaCl, 0.05% Tween-20) for 1 h at room temperature. Antibody solutions (in TBS-T) were added for 1 h at room temperature [monoclonal mouse anti-actin first antibody (Amersham-Pharmacia, Bukinghamshire, UK) and second horseradish peroxidase-coupled antibody (Chemicon, Temecula, Calif.)]. Blots were developed using the ECL system (Amersham-Pharmacia, Bukinghamshire, UK) and the band intensities were quantified by PC-based image analysis (Image Analysis Inc., Ontario, Canada) [19].

Immunoprecipitation, Kinase Assays and Immunoblotting Analysis

Testosterone-BSA or DHT-treated, as well as untreated (control) cells were washed three times with ice-cold PBS and suspended in cold lysis buffer containing 1% Nonidet P-40, 20 mM Tris pH 7.4 and 137 mM NaCl, supplemented with protease and phosphatase inhibitors. Cleared lysates were preadsorbed with protein A-Sepharose for 1 h at 4° C., centrifuged and the supernatants (equal amounts of protein) were subjected to immunoprecipitation using the indicated antibodies and the protein A-Sepharose beads.

The lipid kinase activity of PI-3 kinase was measured by the method of Auger et al [20] with minor modifications. Protein A-Sepharose beads containing immunoprecipitated phosphotyrosine proteins were washed three times with Buffer A (20 mM Tris pH 7.4, 137 mM NaCl, 1 mM $CaCl_2$, 1 mM $MgCl_2$, 1% Nonidet P-40, 0.1 mM $Na_3VO_4$), three times with 5 mM LiCl in 0.1 M Tris (pH 7.4) and twice with TNE (10 mM Tris pH 7.4, 150 mM NaCl, 5 mM EDTA, 0.1 mM $Na_3VO_4$). The immunoprecipitates were then resuspended in TNE and the PI-3 kinase activity was assayed using 0.2 mg/ml phosphatidylinositol-4,5-bisphosphate (PI-4,5-P2) as a substrate, in the presence of 58 M ATP, 10 Ci of [—$^{32}$P]ATP (5000 Ci/mmol) and 14 mM $MgCl_2$, for 10 min at 37° C. The reaction was stopped by the addition of 1 M. HCl and methanol/chloroform (1/1) After mixing vigorously and centrifuging to separate the phases, the lipids in the organic lower phase were separated by TLC on oxalated silica gel 60 sheets, as described [21]. Chromatographed lipids were also visualized by iodine staining and compared to the migration of known standards.

For immunoblot analysis, the cell lysates or the immunoprecipitates were suspended in Laemmli's sample buffer and separated by SDS-PAGE. Proteins were transferred onto nitrocellulose membrane, and the membrane was blocked with 5% nonfat dry milk in TBS-T (20 mM Tris pH 7.6, 137 mM NaCl, 0.05% Tween-20) for 1 h at room temperature. Antibody solutions (in TBS-T containing 5% nonfat dry milk) were added overnight at 4° C. (first antibody) and for 1 h (second horseradish peroxidase-coupled antibody). Blots were developed using the ECL system and the band intensities were quantified by PC-based image analysis (Image Analysis Inc., Ontario, Canada).

Affinity Precipitation

Affinity precipitation with GST-PBD was performed using an assay based on the method of Benard et al [22]. Cells were lysed in $Mg^{2+}$ lysis buffer (MLB), that was provided by the assay kit (UBI, Lake Placid, N.Y.), were mixed with 8 g GST-PBD bound to glutathione-Agarose and incubated for 1 h at 4° C. Precipitates were washed three times with MLB and suspended in Laemmli's sample buffer. Proteins were separated by 11% SDS-PAGE, transferred onto nitro-cellulose membrane, and blotted with anti-Cdc42 or anti-Rac antibody.

In Vivo Effect of Testosterone-BSA in Nude Mice

Nude mice were injected in the back with $5 \times 10^6$ LNCaP cells diluted in Matrigel® (Sigma, St Louis, Mo.) in a total volume of 0.1 ml. After 4 weeks, macroscopical tumors were developed, and treatment was initiated, as follows: Drugs, diluted in PBS were injected intraperitoneally 3 times per week, in a total volume of 0.5 ml. Animals were divided in four groups: The first group received $5 \times 10^{-6}$ M BSA. The second group was injected with $5 \times 10^{-6}$ M testosterone-BSA conjugate. The third group was injected with 10 mg/ml Taxol®, while in the fourth group a combination of testosterone-BSA and Taxol® was introduced. Tumors were measured after four weeks of treatment. Tumors were excised, measured, weighted and send to a pathologist for further analysis.

Results

Membrane Androgen Binding Sites on the Human Prostate Cancer Cell Line LNCaP

Figure 1:
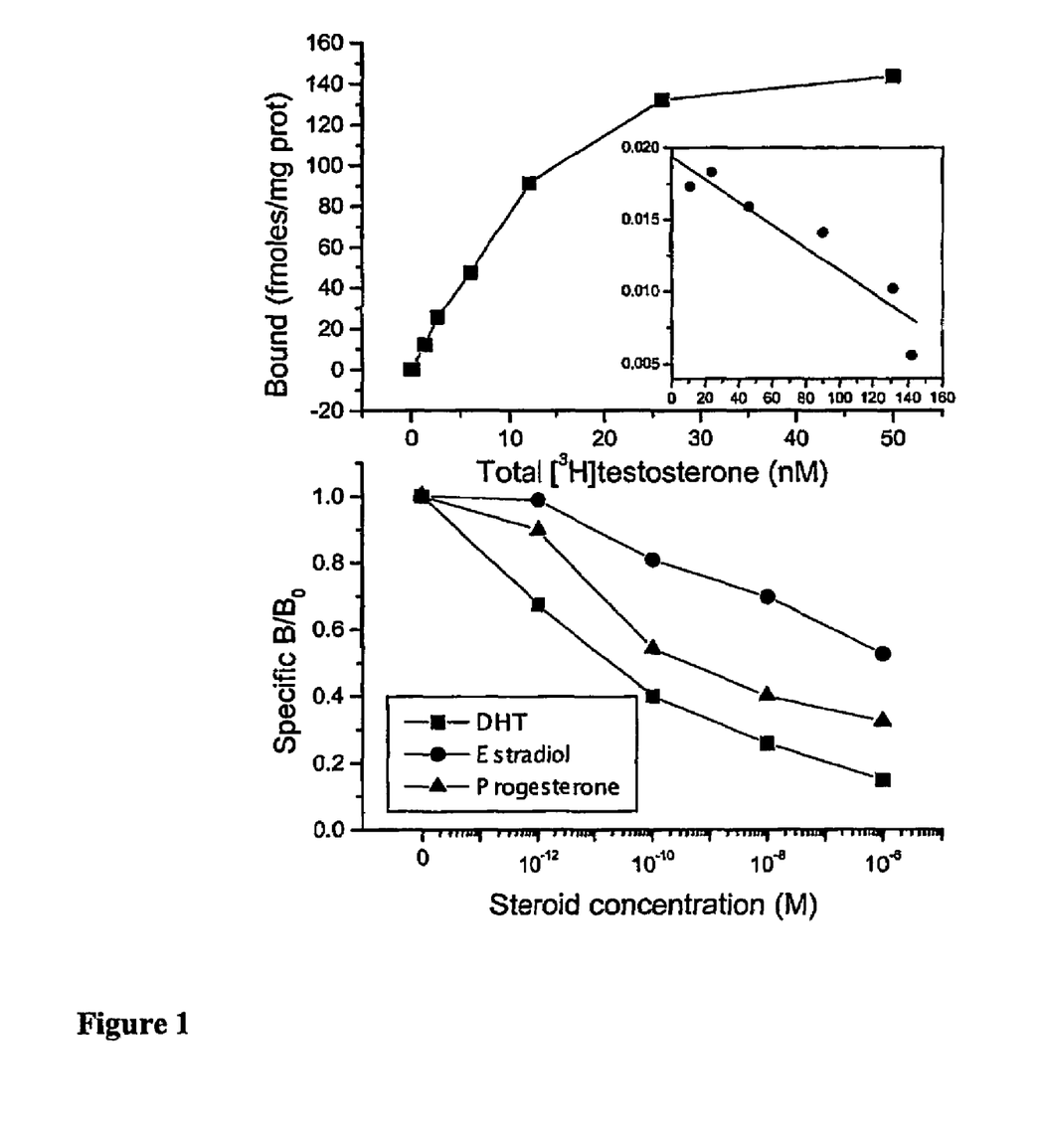
FIG. 1 presents the binding and selectivity characteristics of membrane testosterone receptors in LNCaP cells.
Figure 5:
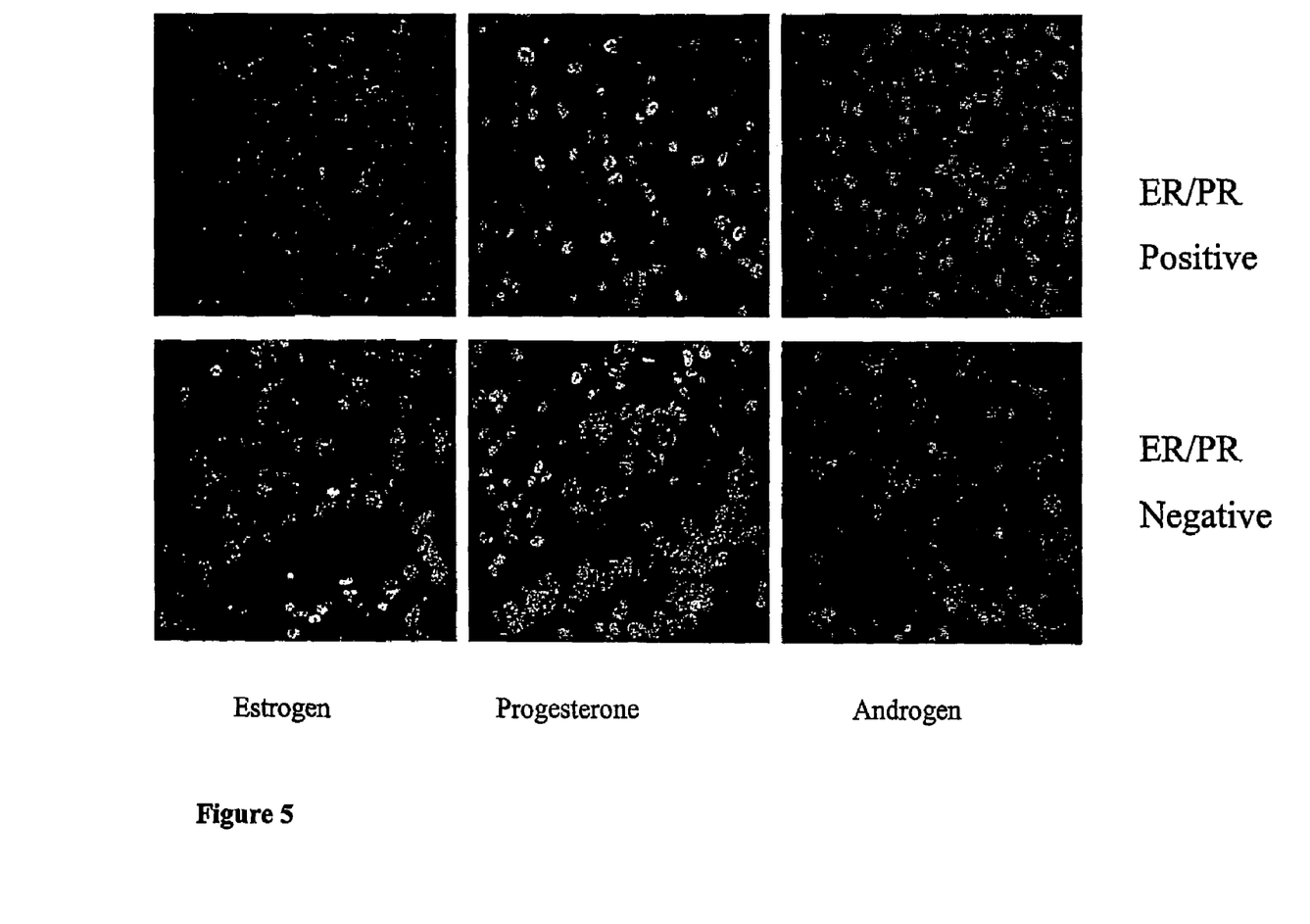
FIG. 5 presents the detection of estrogen, progesterone and androgen receptors in ER positive (upper lane) and ER negative breast cancer.

Membranes, prepared from cultures of LNCaP cells were incubated with different concentrations of [$^3$H]testosterone (ranging 2-50 nM) without (total binding) or with (non-specific binding) a 1000-fold molar excess of unlabelled androgen (DHT). After overnight incubation at 4° C., membrane-bound radioactivity was separated and counted. It was found, as presented in FIG. 1A, that [$^3$H]testosterone, ranging from 1 to 50 nM, induces a specific saturable binding. Scatchard analysis of the results (FIG. 5A insert) revealed a high binding affinity for testosterone ($K_D$ 10.9 nM) and a number of binding sites of 144.3 fmoles/mg protein, corresponding to an approximate number of 13340 sites/cell.

The androgen selectivity of this membrane-binding component was verified by competition displacement experiments. Membranes were incubated with [$^3$H]testosterone in the presence of varying concentrations of DHT or other steroids ($10^{-12}$-$10^{-6}$ M). As shown in FIG. 1B, DHT produced a displacement of radiolabeled testosterone. In contrast, estradiol and progesterone displaced radiolabelled testosterone with a significant lower affinity ($10^4$- and $10^2$-fold respectively) confirming the androgen selectivity of the identified membrane-binding site.

Figure 2:
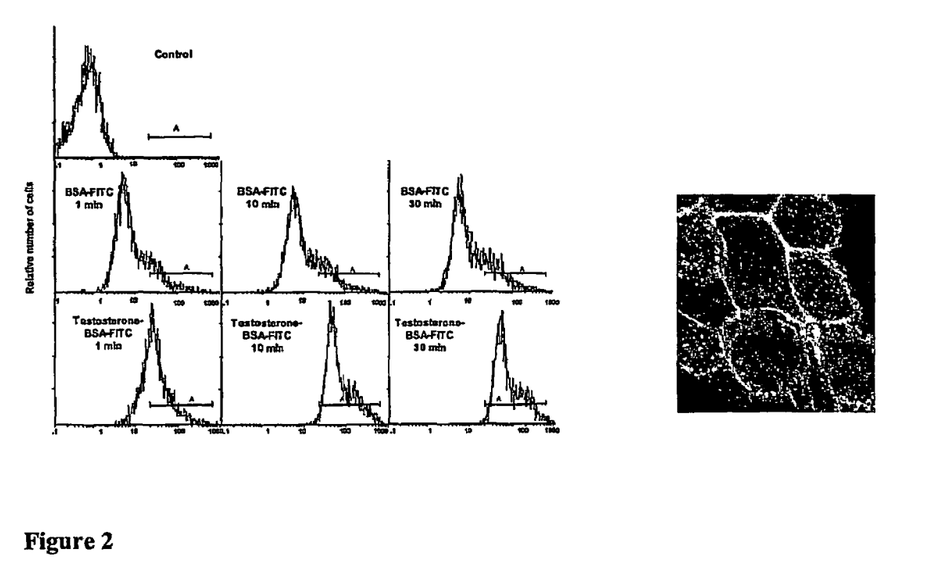
FIG. 2 shows the detection of membrane testosterone receptors, in LNCaP cells by flow cytometry (left panel) and confocal laser scanning microscopy (right panel).

The presence of membrane testosterone receptors was equally identified using the testosterone analog testosterone3-(O-carboxymethyl)oxime-BSA-FITC, obtained from Sigma (St Louis, Mo.). This analog is not capable to penetrate the cells, because of a covalent attachment of the steroid with BSA. As shown in FIG. 2, left panel, a specific membrane binding of testosterone-BSA was found, by flow cytometry, on membranes of LNCaP cells. The association of testosterone-BSA with membrane receptors was observed at 1 min, was maximal after 10 min, and remained unchanged after 30 min of incubation. The membrane binding was equally verified by confocal laser microscopy, as shown in the right panel of FIG. 2. As shown, only membrane staining was found by the use of the testosterone-BSA conjugate, ruling out the hypothesis of a possible internalization of the compound.

From these experiments it was concluded that prostate cancer cells possess specific, high affinity membrane binding sites, which are selective for androgens.

Identification of Membrane Testosterone Receptors in Specimens of Prostate Cancer.

Figure 3:
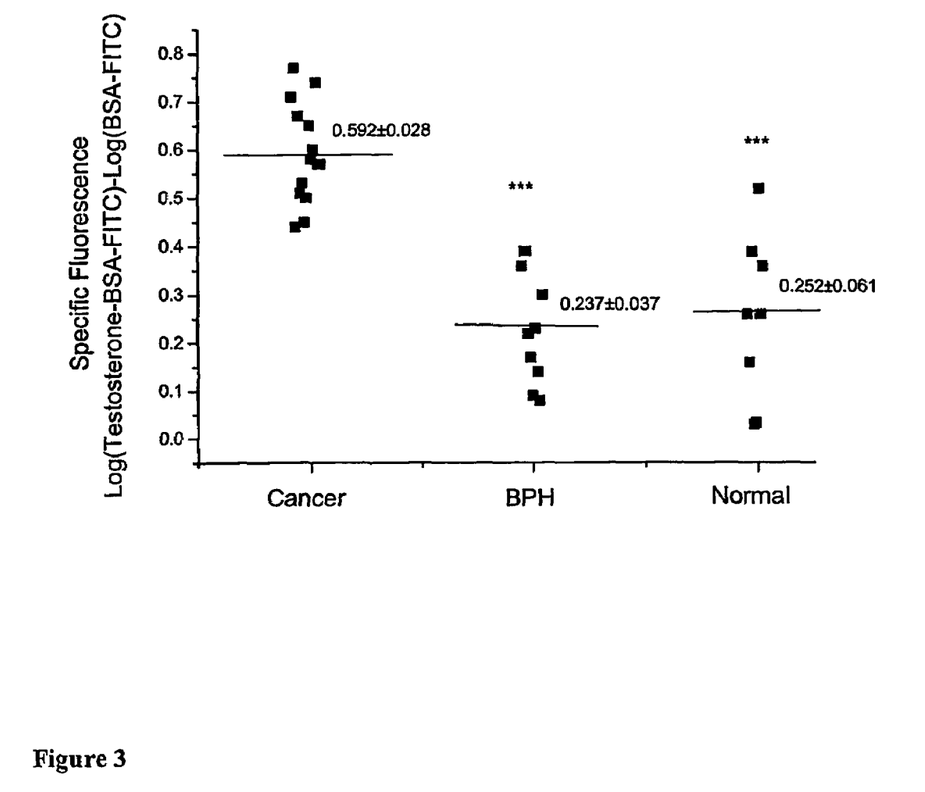
FIG. 3 shows the detection of testosterone membrane receptors (by flow cytometry) in cases of prostate cancer, benigh prostate hyperplasia (BPH) and peritumoral non-tumor cells.

In a series of 14 prostate cancer specimens, 10 transurethral resections for benign prostate hyperplasia (BPH), and 8 microscopically verified non-malignant specimens from the same cases, we have prepared epithelial cell specimens. Cells were immunostained with monoclonal antibodies to vimentine, cytokeratine and PSA, to evidence stromal, and normal or malignant epithelial cells respectively. It was verified that epithelial cells accounted for more than 85% of total cells, in all studied specimens. Cells were incubated for 10 min with testosterone-BSA and assayed by flow cytometry. As shown in FIG. 3, membrane testosterone binding was very low in cases of BPH, while a high binding was found in all cases with cancer. In this respect, membrane testosterone receptors can fully discriminate malignant from benign cases of prostate tumors.

Figure 4:
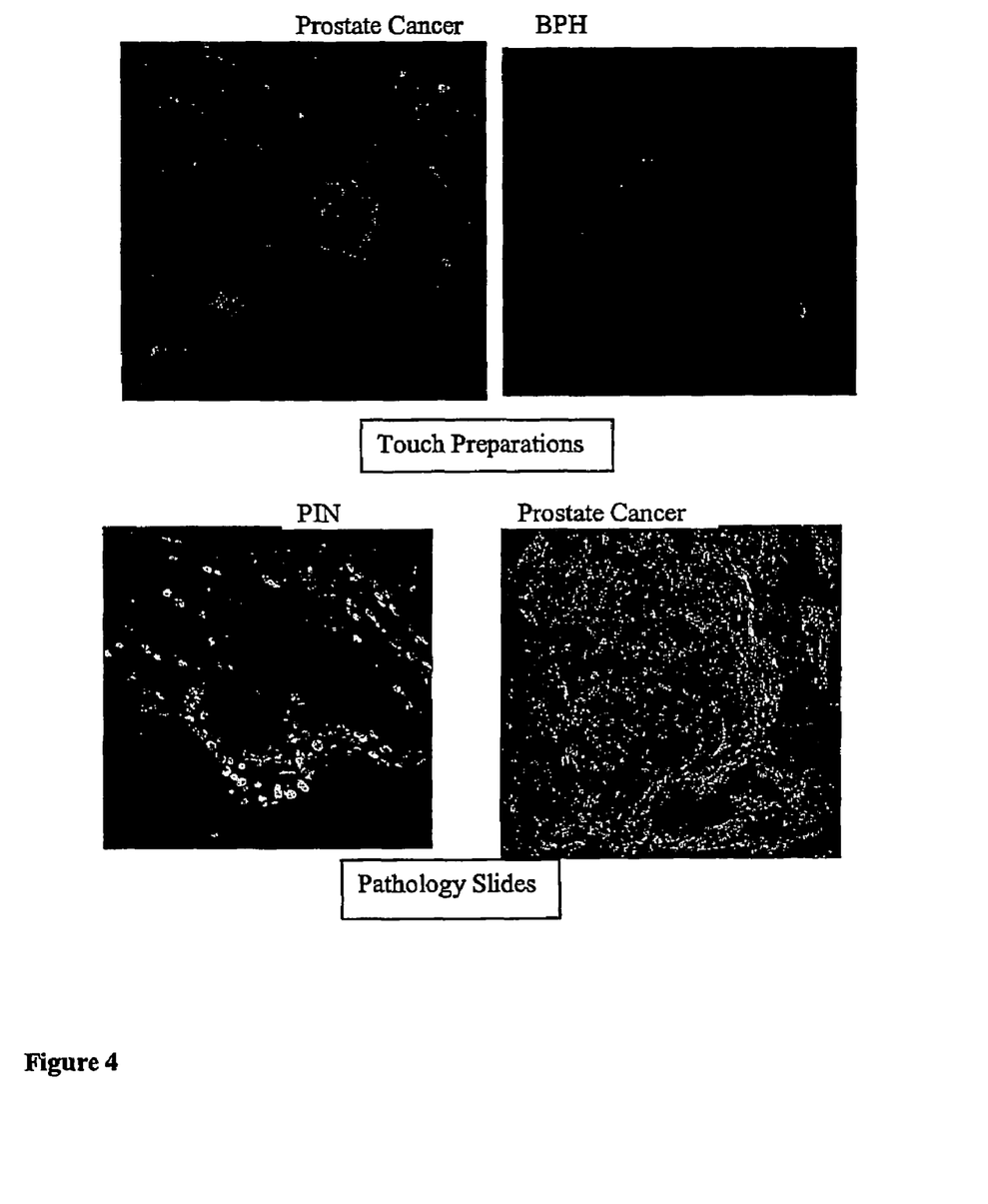
FIG. 4 presents the detection of membrane testosterone receptors in touch preparations of prostate tumors (prostate cancer at the left and BPH at right) and histological slides of prostate intraepithelial neoplasia (PIN, at left) and prostate cancer (right).

The above discrimination was apparent also by fluorescent staining of prostate epithelial cells in touch preparations (FIG. 4, upper panel). Indeed, after surgery, gross identified malignant lesions of the surgical preparations were touched on SuperFrost/Plus slides, adhered cells were stained with testosterone-BSA-FITC, and immediately analysed in a fluorescent microscope. As shown, only malignant epithelial cells were stained, while BPH epithelial cells presented a very low fluorescence. Finally, as shown in the lower panel of FIG. 4, membrane testosterone receptors can be identified in routine histological slides, from formalin-fixed, paraffin-embedded cases of prostate cancer. It is interesting to note further, that testosterone membrane staining can identify cases of intraepithelial neoplasia specifically.

From the above results, it becomes apparent that testosterone membrane receptors are a specific and selective element of prostate cancer.

Identification of Membrane Steroid Receptors in Breast Cancer Specimens

Estrogen-progesterone- and androgen-membrane binding was assayed in steroid receptor positive and negative tumors, as assayed by immunocytochemistry. Typical results are presented in FIG. 5. As shown, regardless of the state of intracellular steroid receptors, BSA-conjugated steroids identify components in histological preparations. Androgen receptors are present in low concentrations in these breast tumors. In contrast, estradiol-BSA and progesterone-BSA identify pericellular components in tumoral cells in the breast. This is more obvious in ER/PR negative tumors, in which there is no interaction with intracellular receptors. Indeed, in ER/PR positive cases, as there is a cellular damage, during slide preparation, these exist, in some cases, a diffuse pattern of staining, which, in some cases can not be attributed to a pericellular, intracellular, or nuclear binding.

Identification of Membrane Steroid Receptors in Hematological Malignancies

In normal blood white blood cells (WBC) we have identified testosterone membrane binding (performing routine flow cytometric assays). The distribution of testosterone-positive cells are shown in Table 1.

TABLE 1

Distribution of membrane testosterone positive (Testo+) cells in different groups of WBC in 20 health blood donors.

| | Lymphocytes | Monocytes | Polymorphonuclear |
|---|---|---|---|
| % of total WBC | 35.6 ± 1.03 | 7.7 ± 0.41 | 56.1 ± 1.18 |
| Testosterone + | 8.9 | 2.2 | 11.6 |
| % Testo+ in category | 23 | 28 | 20 |

As shown, membrane testosterone receptors are expressed in all three classes of WBC. It is interesting that monocytes express, in higher percentages these sites.

The analysis of testosterone membrane receptor in subclasses of lymphocytes is expressed in Table 2.

TABLE 2

Distribution of membrane testosterone positive cells in different categories of lymphocytes. T cells were assayed by the assay of CD3 marker, B by the expression of CD19, and NK cells by the expression of CD56 lymphocyte antigen. Coexpression of the above marker (marked by a PE-labeled monoclonal antibody) with testosterone-BSA-FITC was used for the detection of the testosterone positive subset of cells.

|  | T | B | NK |
|---|---|---|---|
| % of total Lymphocytes | 76 | 14 | 9.7 |
| Testosterone + | 18 | 4.25 | 3.4 |
| % Testo+ in category | 23 | 30 | 34 |

As shown, B-lymphocytes and NK cells express preferentially the testosterone receptor, as compared to T-lymphocytes. In addition, further analysis of T-cells, showed an equal distribution in CD4 and CD8 positive lymphocytes.

In four cases of malignancies, the distribution of testosterone membrane receptor is shown in Table 3.

TABLE 3

Detection of membrane testosterone binding in four cases of hematological malignancies. The mean of the normal controls is given for comparison.

| Diagnosis | Lymphocytes % | % Testo+ | Monocytes % | % Testo+ | Polymorphonuclear % | % Testo+ |
|---|---|---|---|---|---|---|
| ALL remission | 19 | 24 | 8 | 25 | 73 | 19 |
| ALL | 81 | 16 | 1 | 25 | 18 | 14 |
| AML Remission | 32 | 24 | 10 | 35 | 58 | 27 |
| Malignant Lymphoma | 70 | 19 | 7 | 34 | 23 | 16 |
| Normal | 36 | 25 | 8 | 28 | 57 | 21 |

As shown, membrane testosterone binding was found decreased in lymphocytes in ALL, while it returns to the levels of normal controls in remission. In contrast, in malignant lymphma and AML, increased testosterone membrane binding is found in monocytes, while in ALL and the case of lymphoma studied, polymorphonuclear membrane testosterone receptors are found to be decreased.

In Table 4, it is presented the distribution of testosterone receptors in different subclasses of lymphocytes. As shown, membrane testosterone receptors are equally low in all three subsets of lymphocytes, in the case of ALL, returning to normal values after remission. The same result is also found in the case of AML.

TABLE 4

Distribution of membrane testosterone receptors, in four cases of hematological malignancies. Results obtained in normal blood donors are given for comparison.

| Diagnosis | T % | % Testo+ | B % | % Testo+ | NK % | % Testo+ |
|---|---|---|---|---|---|---|
| ALL remission | 85 | 20 | 35 | 6 | 10 | 3 |
| ALL | 64 | 9 | 5 | 2 | 2 | 0.2 |
| AML Remission | 73 | 13 | 5 | 1 | 15 | 5 |
| Malignant Lymphoma | 90 | 17 | 13 | 4 | 5 | 1 |
| Normal | 76 | 18 | 14 | 4 | 10 | 3 |

Figure 6:
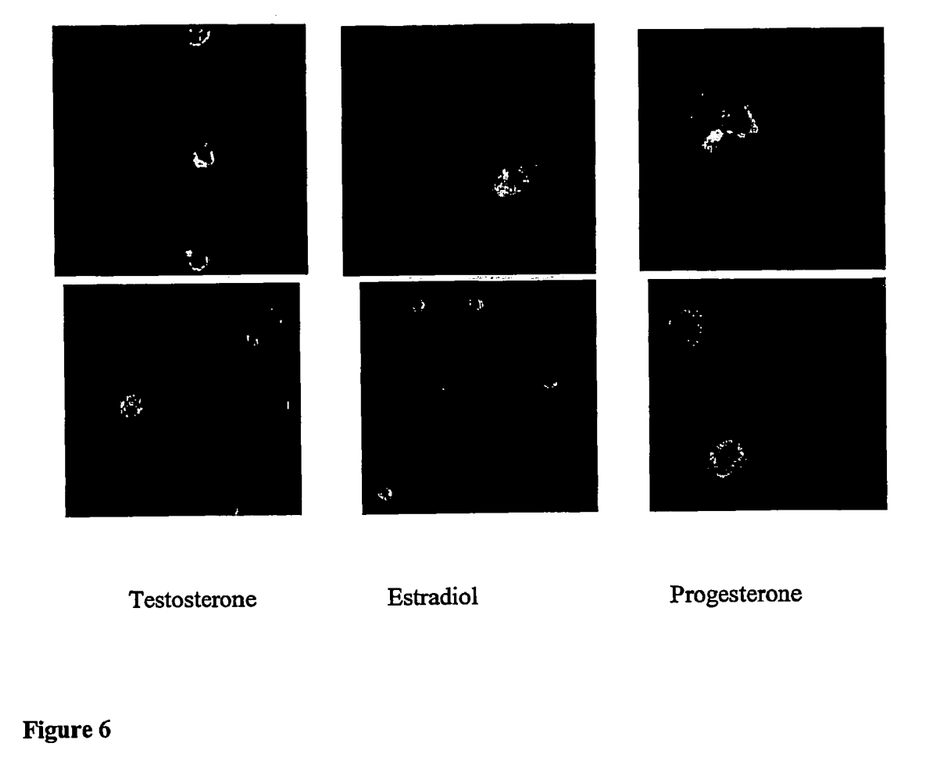
FIG. 6 shows the detection of testosterone, estrogen and progesterone receptors in bone marrow CD34 and AC133 cells (upper and lower lanes).

It is interesting to note that the distribution of testosterone membrane sites shows a differential distribution in normal and leukemic cells. In addition, as shown in FIG. 6, bone marrow stem cells (both CD34 and AC133 positive) express membrane binding sites for all three steroids tested (estrogen, progesterone and androgen). It is therefore possible that the expression of non-mature lymphoid cells account for the differential expression of membrane testosterone receptors, and therefore, the invention may also be used for the detection and treatment of hematological malignancies.

Interaction of Membrane Steroid Receptors with Actin Cytoskeleton

Figure 7:
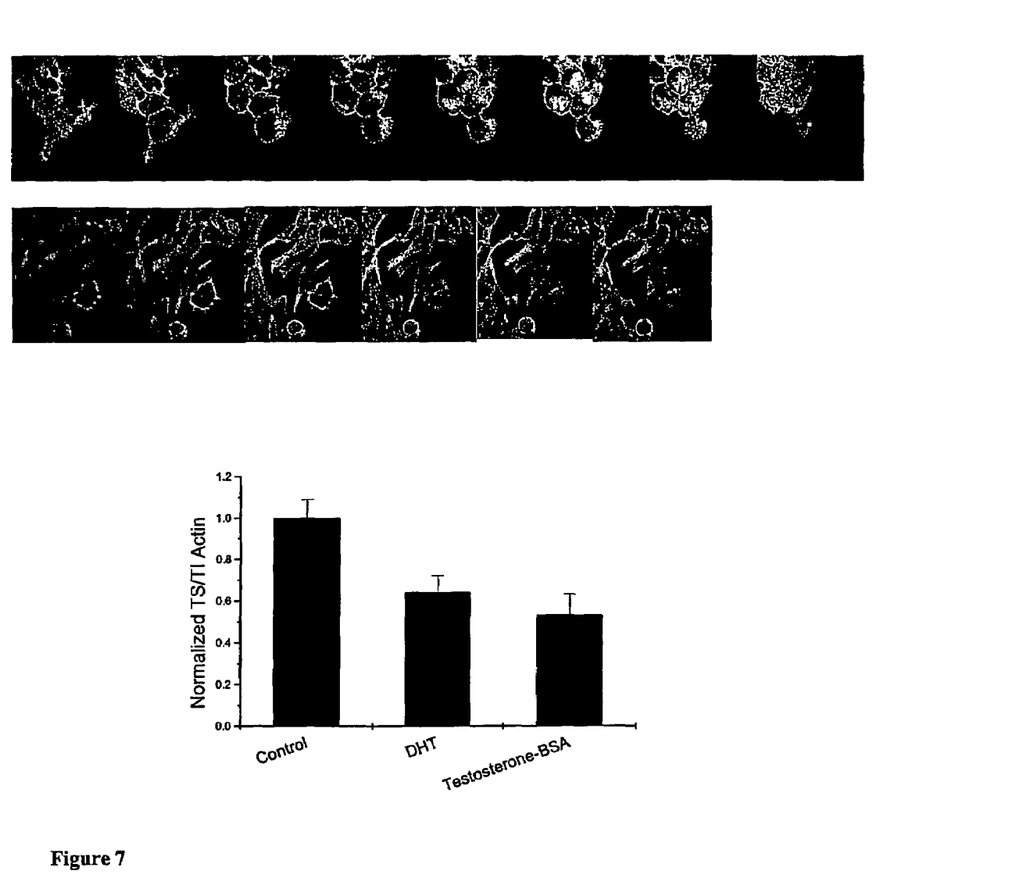
FIG. 7 shows the modification of actin cytoskeleton in LNCaP cells by testosterone-BSA, assayed by confocal scanning laser microscopy (upper panels) and the increase of polymerized actin by testosterone-BSA, assayed by biochemical methods (lower panel).

FIG. 7 shows the effect of action of testosterone-BSA conjugate to the actin cytoskeleton of LNCaP human prostate cancer cells, assayed by confocal laser scanning microscopy. As depicted, 10 minutes after testosterone application, a profound modification of the cytoskeleton occurs. Actin filaments are redistributed at the periphery of the cell, while, as presented at the lower panel of FIG. 7, the significant decrease of the ratio of soluble (monomeric) to insoluble (polymerised) actin indicates that profound alterations of the actin cytoskeleton occur, in favor of a polymerisation process.

Further work revealed that testosterone receptors located on cell membranes of LNCaP cells activate key signalling molecules in a hierarchy of FAK→PI-3 kinase→Cdc42/Rac1→actin reorganization. The fact that testosterone was less active than testosterone-BSA conjugate further indicates that this signalling cascade might be specific of the activation of testosterone membrane binding sites. These results outline, for the first time, a signal transduction pathway that was triggered by membrane testosterone receptors in prostate cancer cells and leads to actin reorganization.

Figure 8:
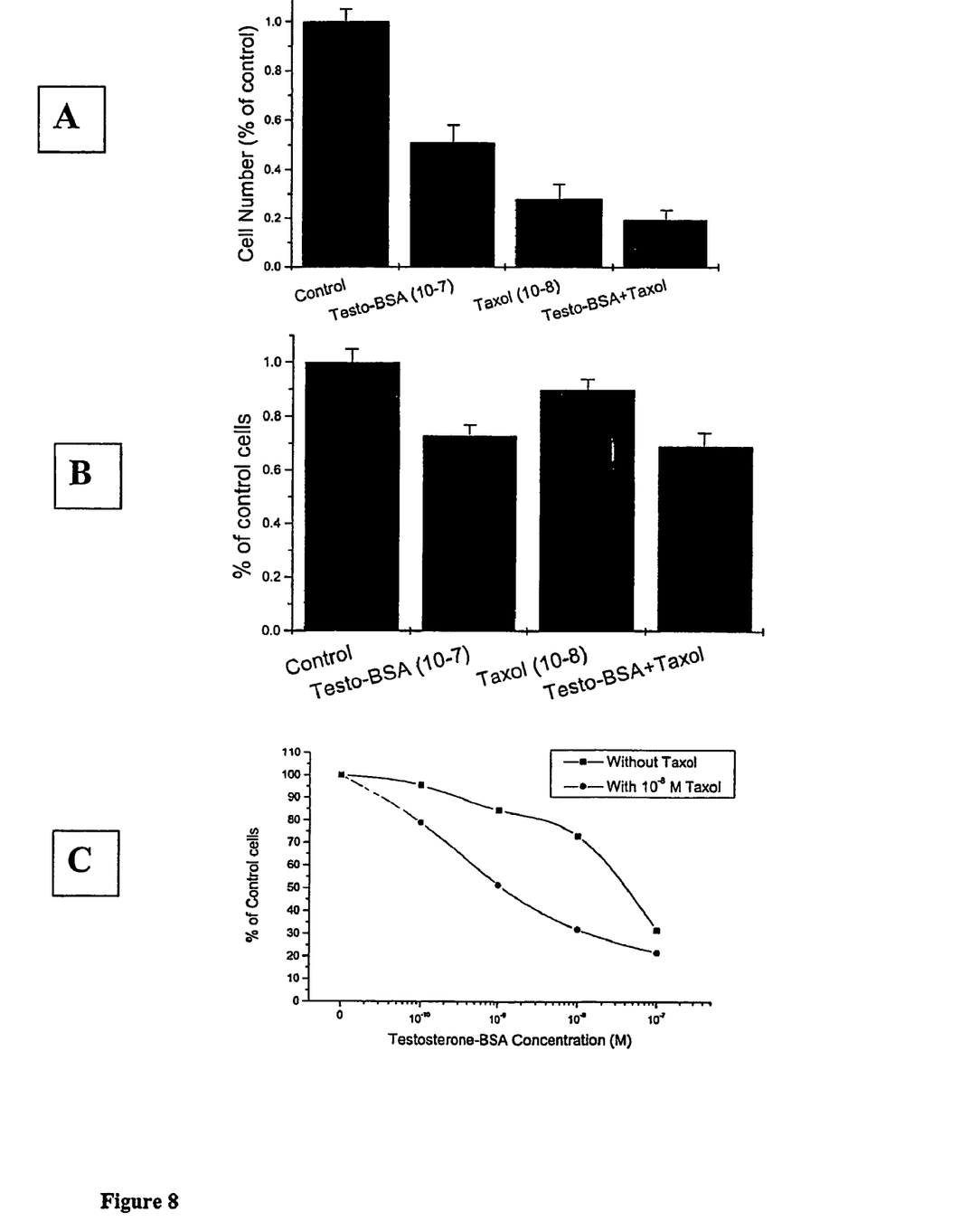
FIG. 8 shows the modification of cell viability by a 24 hour incubation of testosterone-BSA, alone or associated with Taxol® (A), and the effect after an additional incubation of 48 hours, in the absence of drugs (B). Panel C presents the dose-response of cells to testosterone-BSA alone or additioned with Taxol®.

Long Term (24 Hours) Incubation with Testosteroine-BSA Decrease Cell Proliferation of Cancer Cells In view of the above results, we incubated prostate cancer LNCaP cells with testosterone-BSA alone ($10^{-7}$ M) or together with Taxol® ($10^{-8}$ M) for 24 hours. As shown in FIG. 8A, a 50% decrease of cells incubated with testosterone-BSA alone was found. In addition, a potentiation of the action of Taxol® by ~7% was also found. If medium was replaced after this 24 hours incubation, and cells were provided with fresh medium without any added substance and let to stay for additional 48 hours (a condition mimicking the weekly administration of low doses of Taxol® in clinic), cells recover partially (FIG. 8B). In this case, the action of testosterone-BSA is more potent than that of Taxol®. This effect is dose-related to the testosterone-BSA, as shown in FIG. 8C, indicating an additive effect of testosterone-BSA with taxol®.

In Vivo Effects of Testosterone-BSA in Nude Mice

Figure 9:
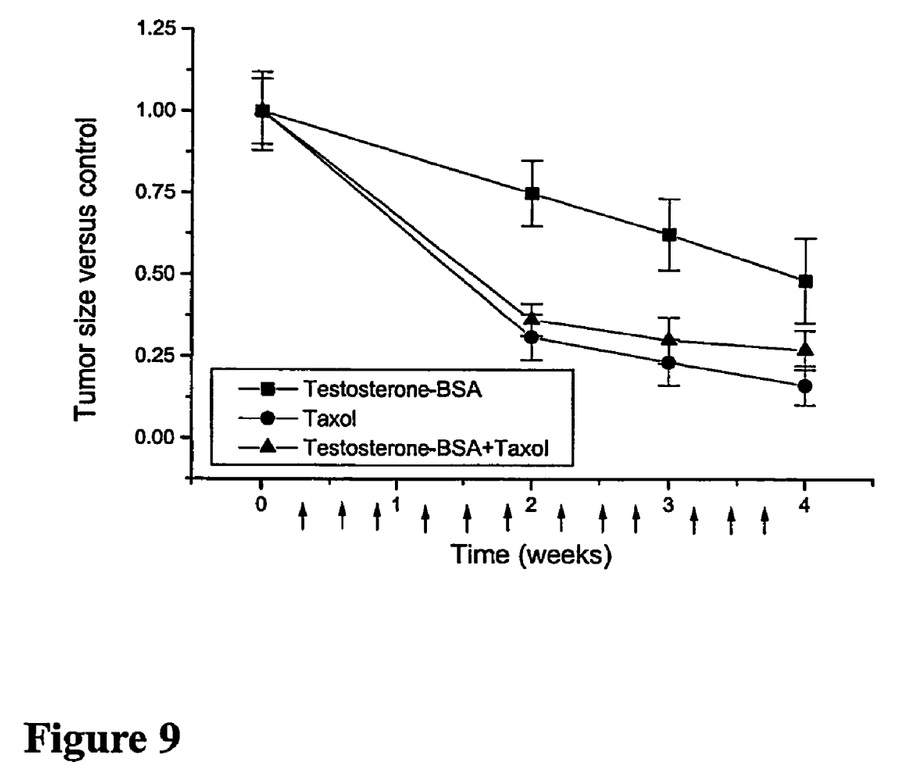
FIG. 9 presents the effect of testosterone-BSA administration in nude mice, bearing implanted tumors. Arrows show the injection times of testosterone-BSA (500 µl of a $5\times10^{-6}$ M solution) with or without addition of 10 mg/kg Taxol®.

All mice supported very well the treatment with testosterone-BSA, at the concentrations used. As presented in FIG. 9, testosterone-BSA induced a time-dependent decrease in tumor mass by 53%. Addition of Taxol® produces a dramatic decrease of tumor weight by 77%. The experiment was stopped at four weeks, while testosterone-BSA did not reach a plateau. Therefore it is possible that the decrease if tumor mass could be greater for longer periods of treatment In addition, apoptosis was observed histologically in all tumors studied.

REFERENCES

1. Brann, D. W., Hendry, L. B. and Mahesh, V. B. (1995) J. Steroid Biochem. Mol. Biol. 52, 113-133.
2. Grazzini, F., Guillon, G., Mouillae, B. and Zinjg, H. H. (1998) Nature 392, 209-512.
3. Wehling, M. (1997) Annu Rev Physiol 59, 365-93.
4. Nadal, A., Rovira, J. M., Laribi, O., Leon-Quinto, T., Andreu, E., Ripoll, C. and Soria, B. (1998) FASEB J. 12, 1341-1348.
5. Nemere, I. and Farach-Carson, M. C. (1998) Biochem. Biophys. Res. Commun. 248, 443-449.
6. Jensen, E. V. (1996) Ann. N.Y. Acad. Sci. 748, 1-17.
7. Kumar, M. V. and Tindall, D. J. (1998) Prog. Nucleic Acid Res. Mol. Biol. 59, 289-306.
8. Benten, P. W., Lieberherr, M., Giese, G., Wrehlke, C., Stamm, O., Sekeris, C., Mossmann, H. and Wunderlich, F. (1999) FASEB J. 13, 123-133.
9. Benten, W. P., Lieberherr, M., Sekeris, C. E. and Wunderlich, F. (1997) FEBS Lett 407, 211-4.
10. Benten, W. P., Lieberherr, M., Stamm, O., Wrehlke, C., Guo, Z. and Wunderlich, F. (1999) Mol Biol Cell 10, 3113-23.
11. Lieberherr, M. and Grosse, B. (1994) J. Biol. Chem. 269, 7217-7223.
12. Gorczynska, E. and Handelsman, D. J. (1995) Endocrinology 136, 2052-9.
13. Armen, T. A. and Gay, C. V. (2000) J Cell Biochem 79, 620-7.
14. Lyng, F. M., Jones, G. R. and Rommerts, F. F. (2000) Biol Reprod 63, 736-47.
15. Koukouritaki, S. B., Margioris, A. N., Gravanis, A., Hartig, R. and Stournaras, C. (1997) J Cell Biochem 65, 492-500.
16. Horoszewicz, J. S., Leong, S. S., Kawinski, E., Karr, J. P., Rosenthal, H., Ming Chu, T., Mirand, E. A. and Murphy, G. P. (1983) Cancer Res. 43, 1809-1818.
17. Mosmann, T. (1973) J. Immunol. Methods 65, 53-63.
18. Bradford, M. M. (1976) Anal. Biochem. 72, 248-254.
19. Golenhofen, N., Doctor, R. B., Bacallao, R. and Mandel, L. J. (1995) Kidney Int 48, 1837-45.
20. Auger, K. R., Serunian, L. A., Soltoff, S. P., Libby, P. and Cantley, L. C. (1989) Cell 57, 167-175.
21. Singh, S. S., Chauhan, A., Murakami, N. and Chauhan, V. P. (1996) Biochemistry 35, 16544-16549.
22. Benard, V., Bohl, B. P. and Bokoch, G. M. (1999) J Biol Chem 274, 13198-13204.

The invention claimed is:

1. A method for treating prostate cancer in a patient comprising administering a compound to the patient, wherein the compound is an androgen steroid covalently attached to a mammalian protein to treat the prostate cancer in the patient.

2. The method of claim 1, wherein the androgen steroid is testosterone.

3. The method of claim 1, wherein the mammalian protein is a recombinant or isolated natural serum albumin.

4. The method of claim 1, wherein the compound is detectably-labeled.

5. The method of claim 2, wherein the testosterone is covalently attached to the mammalian protein through a carboxy-methyl ether linker.

6. The method of claim 5, wherein the linker is covalently attached to the testosterone at the 3' position of the androgen steroid ring.

7. The method of claim 1, wherein the administration of the compound is parenteral, percutaneous or intravenous.

8. The method of claim 1, wherein the compound is administered at least once daily.

9. The method of claim 1, wherein the method further comprises the step of administering an antiandrogen to the patient.

10. The method of claim 1, wherein the method further comprises the step of administering Taxol or Taxotere to the patient.

11. The method of claim 1, wherein the method further comprises the step of decreasing solid cancer mass in the patient.

12. A method for treating prostate cancer in a patient comprising administering to a patient in need thereof a composition,
   wherein the composition comprises a steroid conjugate and an antiandrogen, and wherein said steroid conjugate is an androgen steroid that is covalently bonded to a mammalian protein.

13. The method of claim 12, wherein the antiandrogen is present in about a 10-fold molar excess relative to the molar amount of the androgen steroid.

14. A method for treating prostate cancer in a patient, the method comprising the step of administering to the patient a compound with the following formula: [testosterone-3-(O-carboxymethyl)oxime-serum albumin]; thereby treating the prostate cancer in the patient.

15. The method of claim 14, wherein the method further comprises the step of administering an antiandrogen to the patient.

16. The method of claim 14, wherein the method further comprises the step of administering Taxol or Taxotere to the patient.

17. The method of claim 14, wherein the method further comprises the step of decreasing prostate cancer mass in the patient.

18. A method for treating prostate cancer in a patient comprising administering to a patient in need thereof a composition,
   wherein the composition comprises a steroid conjugate and an antiandrogen, and wherein said steroid conjugate is testosterone-3-(O-carboxymethyl)oxime-serum albumin.

* * * * *